United States Patent
Chon et al.

(10) Patent No.: US 11,185,442 B2
(45) Date of Patent: Nov. 30, 2021

(54) HYBRID PHACOEMULSIFICATION NEEDLE

(71) Applicant: Alcon Inc., Fribourg (CH)

(72) Inventors: James Chon, Irvine, CA (US); Kristine Velasco, Foothill Ranch, CA (US); Rudolph Zacher, Trabuco Canyon, CA (US)

(73) Assignee: Alcon Inc., Fribourg (CH)

( * ) Notice: Subject to any disclaimer, the term of this patent is extended or adjusted under 35 U.S.C. 154(b) by 218 days.

(21) Appl. No.: 16/406,512

(22) Filed: May 8, 2019

(65) Prior Publication Data
US 2019/0262176 A1 Aug. 29, 2019

Related U.S. Application Data

(62) Division of application No. 14/060,826, filed on Oct. 23, 2013, now abandoned.

(51) Int. Cl.
*A61F 9/007* (2006.01)

(52) U.S. Cl.
CPC ................ *A61F 9/00745* (2013.01)

(58) Field of Classification Search
CPC .............. A61F 9/00745; A61F 9/00736; A61F 9/00763; A61F 9/007; A61F 9/008; A61F 2009/0083; A61B 17/320068; A61B 17/320072; A61B 17/22012; A61B 17/3417; A61B 2017/320072; A61B 2017/00477; A61B 2017/22014; A61B 2090/08021; A61B 18/1492; A61B 5/6852; A61M 25/0069; A61M 25/005; A61M 25/001; A61M 25/0045; A61M 25/008; A61M 25/0662; A61M 25/00; A61M 2025/0081; A61M 1/008
See application file for complete search history.

(56) References Cited

U.S. PATENT DOCUMENTS

| | | | |
|---|---|---|---|
| 4,531,934 A * | 7/1985 | Kossovsky | A61F 9/00745 433/91 |
| 4,531,943 A | 7/1985 | Van Tassel et al. | |
| 5,762,637 A * | 6/1998 | Berg | A61M 25/001 604/264 |
| 6,015,403 A * | 1/2000 | Jones | A61F 9/008 606/13 |
| 6,491,670 B1 * | 12/2002 | Toth | A61F 9/007 604/264 |
| 2004/0267211 A1 | 12/2004 | Akahoshi | |

(Continued)

OTHER PUBLICATIONS

Dictionary Definition of Embed from http://www.merriam-webster.com/dictionary/embed accessed on Jun. 10, 2015.

(Continued)

*Primary Examiner* — Mohamed G Gabr

(57) ABSTRACT

A phacoemulsification needle comprises a hollow shaft with an interior surface, an exterior surface, and a distal end terminating in a distal edge. The shaft has a central bore extending there through. The central bore is defined by the interior surface of the hollow shaft. A first over mold is located on the exterior surface and distal edge of the hollow shaft. The first over mold covers at least a portion of a periphery of the exterior surface of the hollow shaft, the distal edge, and terminates at the central bore.

9 Claims, 4 Drawing Sheets

(56) References Cited

U.S. PATENT DOCUMENTS

2009/0048537 A1 2/2009 Lydon et al.
2009/0318746 A1* 12/2009 Thurmond, II ....... A61L 29/041
600/8

OTHER PUBLICATIONS

Dictionary Definition of Huber Needle from http://breastcancer.about.eom/od/hijklterms/g/Huber-Needle-Definition.htm accessed on Jun. 9, 2015 (website updated on Sep. 3, 2013).
Merriam-Webster, Definition of Right Circular Cylinder, accessed on Mar. 29, 2016, <http://www.merriam-webster.com/dictionary/right%20circular%20cylinder>.

* cited by examiner

HYBRID PHACOEMULSIFICATION NEEDLE

RELATED APPLICATIONS

This application is a division of U.S. application Ser. No. 14/060,826 filed on Oct. 23, 2013.

BACKGROUND OF THE INVENTION

This invention relates generally to the field of phacoemulsification and more particularly to phacoemulsification cutting needles.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

In the United States, the majority of cataractous lenses are removed by a surgical technique called phacoemulsification. During this procedure, a thin phacoemulsification cutting needle is inserted into the diseased lens and vibrated ultrasonically. The vibrating cutting needle liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven hand piece, an attached cutting needle, an irrigating sleeve, and an electronic control console. The hand piece assembly is attached to the control console by an electric cable and flexible tubing. Through the electric cable, the console varies the power level transmitted by the hand piece to the attached cutting needle and the flexible tubing supply irrigation fluid to and draw aspiration fluid from the eye through the hand piece assembly.

The operative part of the hand piece is a centrally located, hollow resonating bar or horn directly attached to a set of piezoelectric crystals. The crystals supply the required ultrasonic vibration needed to drive both the horn and the attached cutting needle during phacoemulsification and are controlled by the console. The crystal/horn assembly is suspended within the hollow body or shell of the hand piece by flexible mountings. The hand piece body terminates in a reduced diameter portion or nosecone at the body's distal end. The nosecone is externally threaded to accept the irrigation sleeve. Likewise, the horn bore is internally threaded at its distal end to receive the external threads of the cutting needle. The irrigation sleeve also has an internally threaded bore that is screwed onto the external threads of the nosecone. The cutting needle is adjusted so that the needle projects only a predetermined amount past the open end of the irrigating sleeve.

In use, the ends of the cutting needle and irrigating sleeve are inserted into a small incision of predetermined width in the cornea or sclera. The cutting needle is ultrasonically vibrated along its longitudinal axis within the irrigating sleeve by the crystal-driven ultrasonic horn, thereby emulsifying the selected tissue in situ. The hollow bore of the cutting needle communicates with the bore in the horn that in turn communicates with the aspiration line from the hand piece to the console. A reduced pressure or vacuum source in the console draws or aspirates the emulsified tissue from the eye through the open end of the cutting needle, the cutting needle and horn bores and the aspiration line and into a collection device. The aspiration of emulsified tissue is aided by a saline solution or irrigating solution that is injected into the surgical site through the small annular gap between the inside surface of the irrigating sleeve and the cutting needle.

In some cases, the cutting needle, which is typically made of titanium or stainless steel, may damage eye structures. The distal end of the cutting needle may also sometimes be sharper than is necessary to perform cataract removal. It would be desirable to have a cutting needle that overcomes these shortfalls.

SUMMARY OF THE INVENTION

In one example of the present invention, a phacoemulsification needle comprises a hollow shaft with an interior surface, an exterior surface, and a distal end terminating in a distal edge, the shaft having a central bore extending there through, the central bore defined by the interior surface of the hollow shaft; and a first over mold located on the exterior surface and distal edge of the hollow shaft, the first over mold covering at least a portion of a periphery of the exterior surface of the hollow shaft, the first over mold covering the distal edge and terminating at the central bore.

In other examples of the present invention, the phacoemulsification needle further comprises a through hole located in the hollow shaft and extending from the exterior surface to the interior surface of the hollow shaft wherein the first over mold substantially fills the through hole. The first over mold may have a rounded front edge located over the distal edge of the hollow shaft and a rounded trailing edge located on the exterior surface of the hollow shaft. The first over mold may extend circumferentially around the entire perimeter of the exterior surface of the hollow shaft. The first over mold may be made of a polymer.

In other examples of the present invention, the phacoemulsification needle further comprises a second over mold located on the first over mold, the second over mold covering at least a portion of a periphery of an exterior surface of the first over mold, the second over mold covering the rounded front edge of the first over mold and terminating at the central bore. The second over mold may be embedded in the first over mold such that the exterior surface of the first over mold is continuous with an exterior surface of the second over mold. The second over mold may extend circumferentially around the entire perimeter of the exterior surface of the hollow shaft. The second over mold may be made of silicone.

In another example of the present invention, a method comprises providing a phacoemulsification needle as described in the preceding three paragraphs and causing that needle to be vibrated in the eye, for example, to perform cataract surgery.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference is now made in detail to the exemplary embodiments of the invention, examples of which are illustrated in the accompanying drawings. Wherever possible, the same reference numbers are used throughout the drawings to refer to the same or like parts.

Figure 1:
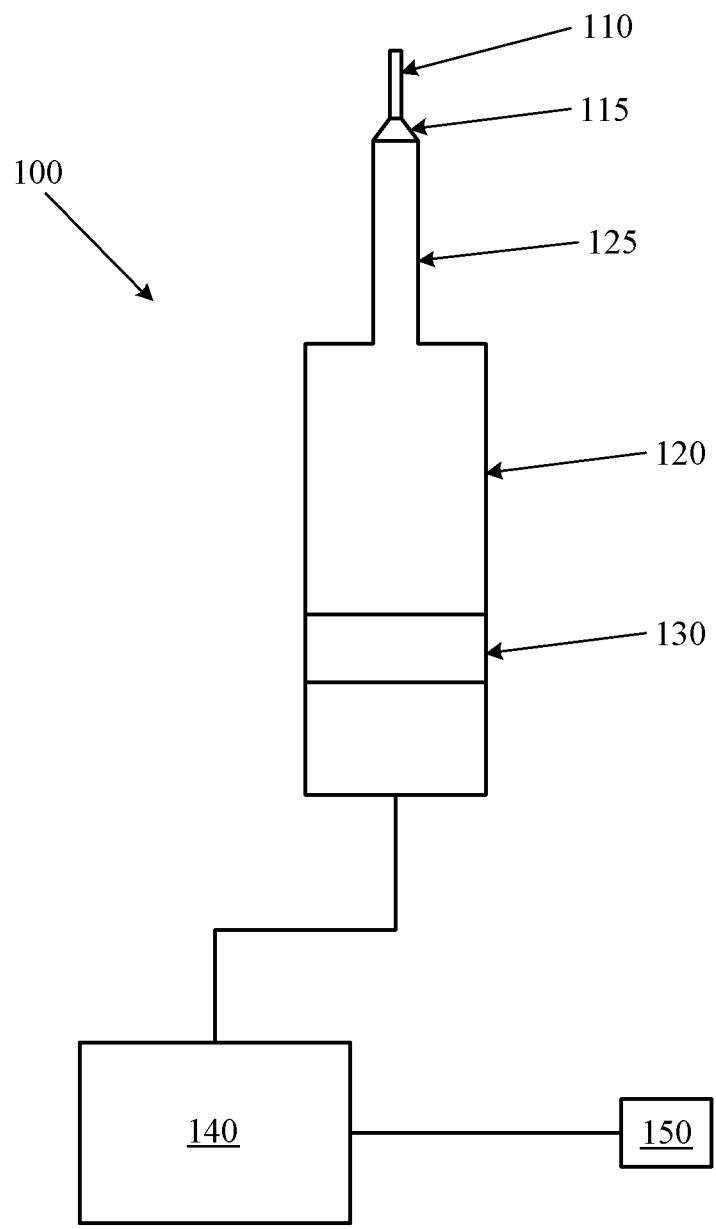
FIG. 1 is a diagram of a phacoemulsification hand piece system.

FIG. 1 depicts an ultrasonic hand piece system. In FIG. 1, hand piece 100 is coupled to console 140. Console 140 is coupled to foot switch 150. Hand piece 100 has a cutting needle 110, a horn 120, and a set of piezoelectric crystals 130. A needle interface 115 connects cutting needle 110 to a reduced diameter portion 125 of horn 120.

Needle 110 is typically a thin needle made of titanium or stainless steel that is designed to emulsify a lens when vibrated ultrasonically. Needle 110 is typically cylindrical in shape, has a small diameter of about 20-30 gauge, and has a length suitable for removal of a lens when inserted into the anterior chamber of the eye.

Horn 120 is typically made of a rigid material suitable for medical use (such as a titanium alloy). Horn 120 has a reduced diameter section 125 that is connected to a needle interface 115. Needle interface 115 typically has a threaded connection that accepts needle 110. In this manner needle 110 is screwed onto horn 120 at needle interface 115. This provides a rigid connection between needle 110 and horn 120 so that vibration can be transmitted from horn 120 to needle 110.

Piezoelectric crystals 130 supply ultrasonic vibrations that drive both the horn 120 and the attached cutting needle 110 during phacoemulsification. Piezoelectric crystals 130 are affixed to horn 120. Crystals 130 are typically ring shaped, resembling a hollow cylinder and constructed from a plurality of crystal segments. When excited by a signal from console 140, crystals 130 resonate, producing vibration in horn 120.

Console 140 includes a signal generator that produces a signal to drive piezoelectric crystals 130. Console 140 has a suitable microprocessor, micro-controller, computer, or digital logic controller to control the signal generator. In operation, console 140 produces a signal that drives piezoelectric crystals 130. Piezoelectric crystals 130, when excited, cause horn 120 to vibrate. Needle 110, connected to horn 120, also vibrates. When needle 110 is inserted into the anterior chamber of the eye and vibrated, it acts to emulsify a cataractous lens.

In cataract surgery, the needle 110 is typically made only of titanium or stainless steel. Because the needle 110 is vibrated in the eye ultrasonically (typically at frequencies greater than 30 kHz), it is important to have a needle 110 that can withstand such vibrations. It had been thought that polymer needles or needles with a polymer over mold would not withstand such vibrating force. The inventors of the present application have discovered that the phacoemulsification needles described and claimed herein withstand such vibrations and function to remove natural lenses during cataract surgery.

Figure 2:
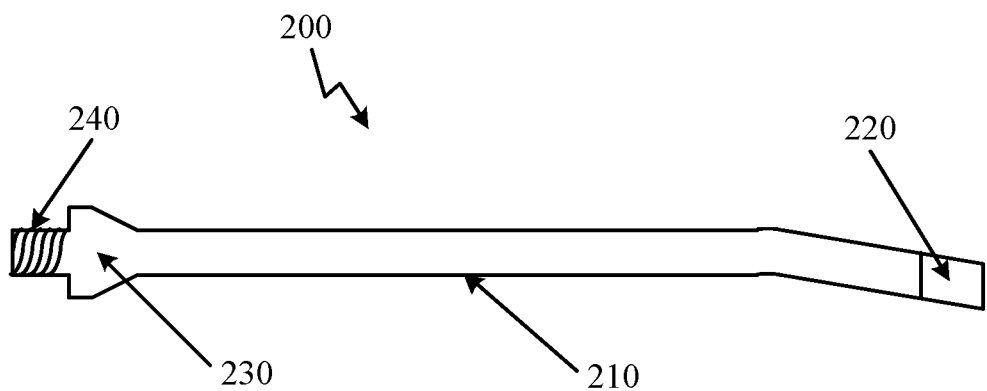
FIG. 2 is a side view of a phacoemulsification needle with a polymer distal end according to an embodiment of the present invention.

FIG. 2 is a side view of a phacoemulsification needle 200 with a polymer distal end according to an embodiment of the present invention. Needle 200 has a shaft 210 terminating at a distal end 220. Opposite the polymer distal end 220 is a hub 230 and threaded connection 240. Shaft 210 is typically cylindrical with a central bore that forms a part of the aspiration path. Fragmented lens particles and irrigating solution are aspirated through the central bore of shaft 210. Hub 230 and threaded connection 240 allow the needle 200 to be coupled to a hand piece. Shaft 210, hub 230, and threaded connection 240 are typically made from titanium, stainless steel or other similar material. As described in greater detail below, distal end 220 may be made of a polymer, plastic, silicone or other similar material. Such materials are generally softer, smoother, and have more rounded edges than the titanium or stainless steel of traditional phacoemulsification needles. As noted, the distal end 220 of phacoemulsification needle 200 is inserted into the eye to remove a cataract. The distal end 220 of phacoemulsification needle 200 also comes into contact with other delicate eye structures. A distal end made of a polymer, plastic, silicone or other similar material tends to damage these delicate eye structures less than a phacoemulsification needle with a distal end made of titanium or stainless steel.

Figure 3:
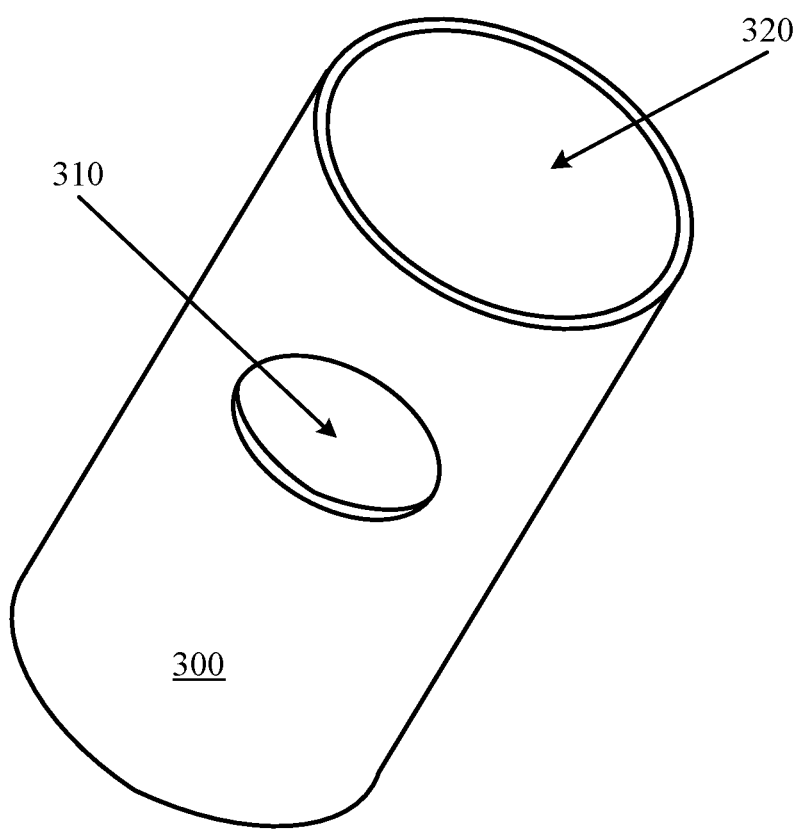
FIG. 3 is a perspective view of the distal end of a phacoemulsification needle according to an embodiment of the present invention.

FIG. 3 is a perspective view of the distal end of a phacoemulsification needle according to an embodiment of the present invention. FIG. 3 depicts the distal end 300 of a phacoemulsification needle with a central bore 320 and a through hole 310 in a side wall of distal end 300. Distal end 300 is typically made of titanium, stainless steel, or other similar material. The through hole 310 allows an over mold to be secured to distal end 300. In some cases, a polymer may be over molded onto distal end 300. Through hole 310 is filled with the polymer and acts to secure it to distal end 300. While through hole 310 is shown as a continuous oval opening in a side wall of distal end 310, through hole may be of any suitable shape. In addition, through hole 310 may have a discontinuous periphery (e.g., serrated) that serves to grip a polymer over mold.

Figure 4:
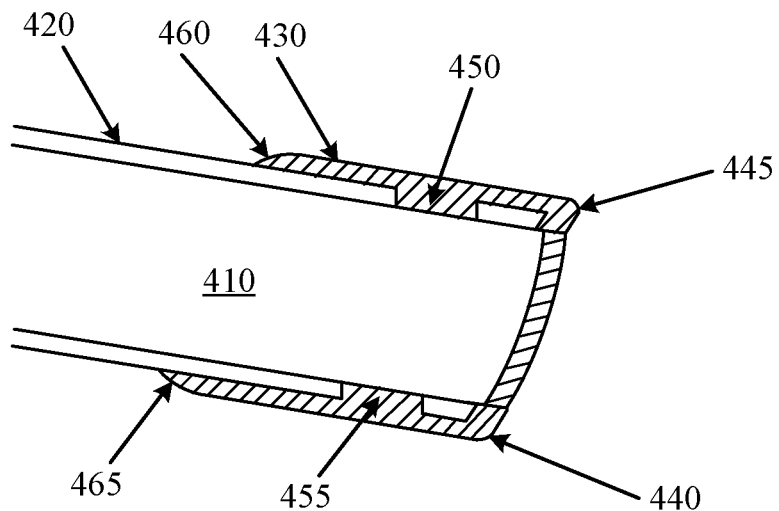
FIG. 4 is a side cross section view of the distal end of a phacoemulsification needle with an over molded distal end according to an embodiment of the present invention.

FIG. 4 is a side cross section view of the distal end of a phacoemulsification needle with an over molded distal end according to an embodiment of the present invention. Over mold 430 (shown as the shaded portion of FIG. 4) is located on shaft 420. Shaft 420 has a continuous central bore that extends to an open end at the distal end of over mold 430. The distal end of over mold 430 has a rounded front edge (440, 445) that extends circumferentially around the perimeter of shaft 420. When shaft 420 is a hollow cylinder, over mold 430 is located around the periphery of the cylinder and covers the edges of the distal end of the cylinder. Typically, a phacoemulsification needle is essentially a metal tube with a wall thickness. The central bore of the metal tube extends completely and continuously through it. The distal end of such a phacoemulsification needle often has sharp edges (or edges that are not rounded). The depth of these edges is defined by the wall thickness of the needle. Over mold 430 would be located on such a phacoemulsification needle around its periphery. Over mold 430 would extend to cover the edges on the distal end of the needle. In this manner, over mold 430 provides a soft, rounded, pliable, and/or smooth surface that covers the sharp edges of the needle and extends back from the distal end of the needle along the needle shaft 420.

Over mold 430 has a rounded or smooth front edge (shown in the cross section drawing as 440 & 445) and a rounded or smooth trailing edge (shown in the cross section drawing as 460 and 465). These front (440, 445) and trailing (460, 465) edges allow for the phacoemulsification needle to be easily inserted into and removed from a small incision in the eye. Because these front (440, 445) and trailing (460, 465) edges are smooth, soft, rounded and/or pliable, over mold 430 better protects delicate eye structures during cataract surgery. In particular, the front edge (440, 445) or over mold 430 is much less likely to damage eye structures than a traditional phacoemulsification needle.

Over mold 430 may be made of a polymer, plastic, silicone or the like. Generally, over mold 430 is molded onto shaft 420 by, for example, an injection molding process. As shown in FIG. 4, two through holes 450 and 455 secure over mold 430 to shaft 420. In other examples of the invention, other structures on shaft 420 (such as protrusions, indentations, or the like) are used to secure over mold 430 to shaft 420. In other examples, no through holes 450, 455 are present, and over mold 430 is secured onto shaft 420 by friction or an adhesive. In one example, over mold 430 is premolded and fixed to shaft 420 by friction or an adhesive. When over mold 430 is injection molded onto shaft 420, a dowel or other similar structure may be placed in central bore 410 to prevent material from entering the central bore 410 through the through holes 450, 455.

Figure 5:
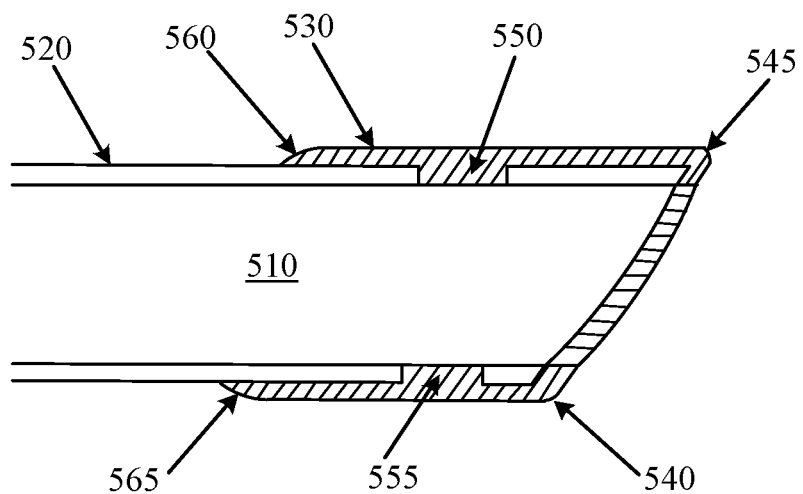
FIG. 5 is a side cross section view of the distal end of a phacoemulsification needle with an over molded distal end according to an embodiment of the present invention.

FIG. 5 is a side cross section view another example of the distal end of a phacoemulsification needle with an over molded distal end according to an embodiment of the present invention. In FIG. 5, the needled is beveled. Over mold 530 (shown as the shaded portion of FIG. 5) is located on shaft 520. Shaft 520 has a continuous central bore that extends to an open end at the distal end of over mold 530. The distal end of over mold 530 has a rounded front edge (540, 545) that extends circumferentially around the perimeter of shaft 520. When shaft 520 is a hollow cylinder, over mold 530 is located around the periphery of the cylinder and covers the edges of the distal end of the cylinder. Typically, a phacoemulsification needle is essentially a metal tube with a wall thickness. The central bore of the metal tube extends completely and continuously through it. The distal end of such a phacoemulsification needle often has sharp edges (or edges that are not rounded) especially when the end of the needle is beveled. The depth of these edges is defined by the wall thickness of the needle. Over mold 530 would be located on such a phacoemulsification needle around its periphery. Over mold 530 would extend to cover the edges on the distal end of the needle. In this manner, over mold 530 provides a soft, rounded, pliable, and/or smooth surface that covers the sharp edges of the needle and extends back from the distal end of the needle along the needle shaft 520.

Over mold 530 has a rounded or smooth front edge (shown in the cross section drawing as 540 & 545) and a rounded or smooth trailing edge (shown in the cross section drawing as 560 and 565). These front (540, 545) and trailing (560, 565) edges allow for the phacoemulsification needle to be easily inserted into and removed from a small incision in the eye. Because these front (540, 545) and trailing (560, 565) edges are smooth, soft, rounded and/or pliable, over mold 530 better protects delicate eye structures during cataract surgery. In particular, the front edge (540, 545) or over mold 530 is much less likely to damage eye structures than a traditional phacoemulsification needle.

Over mold 530 may be made of a polymer, plastic, silicone or the like. Generally, over mold 530 is molded onto shaft 520 by, for example, an injection molding process. As shown in FIG. 5, two through holes 550 and 555 secure over mold 530 to shaft 520. In other examples of the invention, other structures on shaft 520 (such as protrusions, indentations, or the like) are used to secure over mold 530 to shaft 520. In other examples, no through holes 550, 555 are present, and over mold 530 is secured onto shaft 520 by friction or an adhesive. In one example, over mold 530 is premolded and fixed to shaft 520 by friction or an adhesive. When over mold 530 is injection molded onto shaft 520, a dowel or other similar structure may be placed in central bore 510 to prevent material from entering the central bore 510 through the through holes 550, 555.

Figure 6:
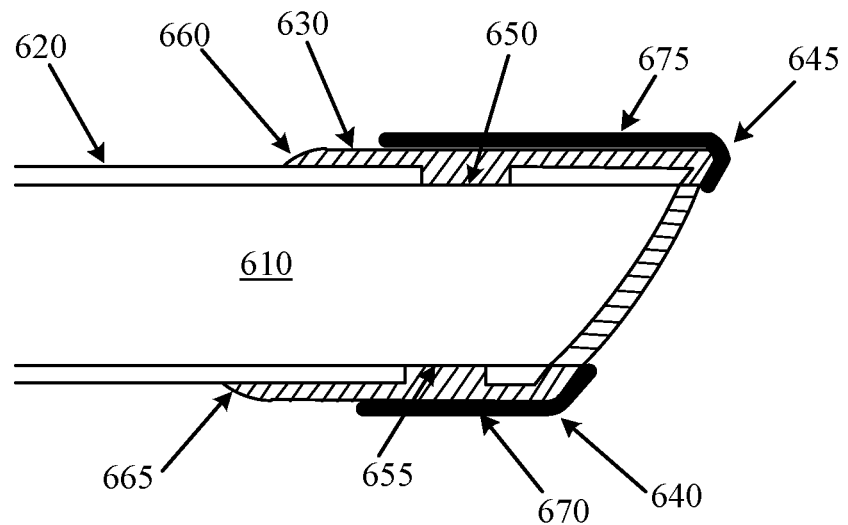
FIG. 6 is a side cross section view of the distal end of a phacoemulsification needle with an over molded distal end according to an embodiment of the present invention.
Figure 7:
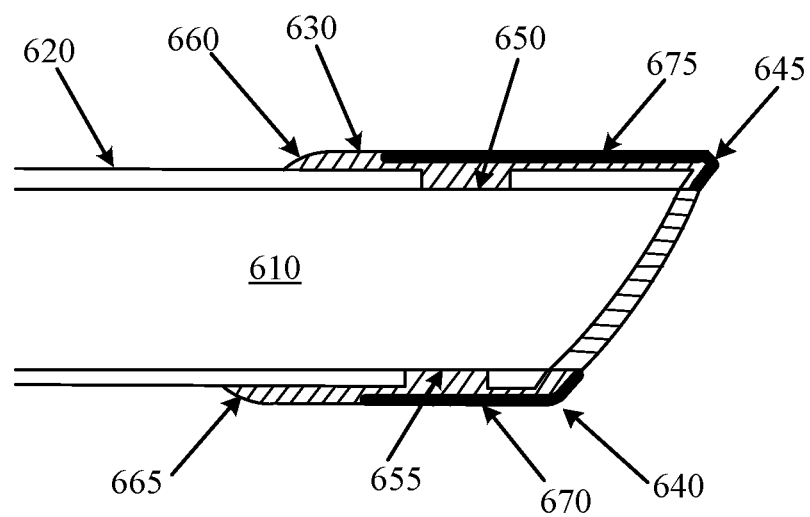
FIG. 7 is a side cross section view of the distal end of a phacoemulsification needle with an over molded distal end according to an embodiment of the present invention.

FIGS. 6 and 7 are side cross section views of the distal end of a phacoemulsification needle with an over molded distal end according to an embodiment of the present invention. In FIGS. 6 and 7, a first over mold 630 and a second over mold (570, 575) are present on the distal end of shaft 620. First over mold 630 (shown as the shaded portion of FIG. 6) is located on shaft 620. Shaft 620 has a continuous central bore that extends to an open end at the distal end of first over mold 630. The distal end of first over mold 630 has a rounded front edge (640, 645) that extends circumferentially around the perimeter of shaft 620. When shaft 620 is a hollow cylinder, first over mold 630 is located around the periphery of the cylinder and covers the edges of the distal end of the cylinder. Typically, a phacoemulsification needle is essentially a metal tube with a wall thickness. The central bore of the metal tube extends completely and continuously through it. The distal end of such a phacoemulsification needle often has sharp edges (or edges that are not rounded) especially when the end of the needle is beveled. The depth of these edges is defined by the wall thickness of the needle. First over mold 630 would be located on such a phacoemulsification needle around its periphery. First over mold 630 would extend to cover the edges on the distal end of the needle. In this manner, first over mold 630 provides a soft, rounded, pliable, and/or smooth surface that covers the sharp edges of the needle and extends back from the distal end of the needle along the needle shaft 620.

A second over mold 670, 675 is located on first over mold 630. Second over mold 670, 675 may cover all or a portion of first over mold 630. In one example, second over mold 670, 675 is silicone which provides a smooth and pliable surface that does not cause unwanted damage to eye structures. In this case, the second over mold 670, 675 may be applied to first over mold 630 in a two shot molding process, by an adhesive, or by other similar means. In the example shown in FIGS. 6 and 7, second over mold 670, 675 extends along shaft 620 and covers the distal edge of first over mold 630. In such a case, the sharp edges of the distal end of shaft 620 are covered by the material of first over mold 630 and the material of second over mold 670, 675. In the example of FIG. 6, the second over mold 670, 675 is applied on top of first over mold 630. In the example of FIG. 7, second over mold 670, 675 is embedded in first over mold 630 such that the outer surface of first over mold 630 and second over mold 670, 675 form a smooth, continuous surface.

First over mold 630 and second over mold 670, 675 have rounded or smooth front edges 640, 645. First over mold has a rounded or smooth trailing edge (shown in the cross section drawing as 660 and 665). These front (640, 645) and trailing (660, 665) edges allow for the phacoemulsification needle to be easily inserted into and removed from a small incision in the eye. Because these front (640, 645) and trailing (660, 665) edges are smooth, soft, rounded and/or pliable, first over mold 630 and second over mold 670, 675 better protect delicate eye structures during cataract surgery. In particular, the front edge (640, 645) or first over mold 630 and second over mold 640, 645 are much less likely to damage eye structures than a traditional phacoemulsification needle.

First over mold 630 may be made of a polymer, plastic, silicone or the like. Generally, first over mold 630 is molded onto shaft 620 by, for example, an injection molding process. As shown in FIG. 6, two through holes 650 and 655 secure first over mold 630 to shaft 620. In other examples of the invention, other structures on shaft 620 (such as protrusions, indentations, or the like) are used to secure first over mold 630 to shaft 620. In other examples, no through holes 650, 655 are present, and first over mold 630 is secured onto shaft 620 by friction or an adhesive. In one example, first over mold 630 is premolded and fixed to shaft 620 by friction or an adhesive. When first over mold 630 is injection molded onto shaft 620, a dowel or other similar structure may be placed in central bore 610 to prevent material from entering the central bore 610 through the through holes 650, 655.

In operation, any of the needles 430, 530, or 630 can be secured to a phacoemulsification hand piece via a threaded connection 240. The needle 430, 530, or 630 is then inserted into the anterior chamber of the eye through a small incision and vibrated ultrasonically. Lens material and fluid are aspirated through the central bore 410, 510, or 610 of the respective needle 430, 530, or 630. Over mold 430, 530, or 630 is secured to the needle such that the ultrasonic vibrations do not cause it to move. In other words, the over mold is subjected to the stresses of vibration and surgery without being dislocated from the needle. In addition, the front edge of the over mold protects delicate eye structures from the unintended stresses of surgery. For example, the over mold is rigid enough to fracture a natural lens but smooth enough not to damage the posterior lens capsule. When a second over mold is present, the first and second over molds operate cooperatively.

From the above, it may be appreciated that the present invention provides an improved phacoemulsification needle for cataract surgery. The present invention provides a phacoemulsification needle with a polymer distal end. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method comprising:
   providing a phacoemulsification needle comprising:
   a rigid hollow shaft with an interior surface, an exterior surface, and a distal end terminating in a rigid distal edge, the shaft having a central bore extending there through, the central bore defined by the interior surface of the hollow shaft; and
   a first over mold located on the exterior surface and distal edge of the hollow shaft, the first over mold covering at least a portion of a periphery of the exterior surface of the hollow shaft, the first over mold covering the distal edge and terminating at the central bore; and
   causing the phacoemulsification needle to be ultrasonically vibrated in the eye to emulsify a cataract.

2. The method of claim 1 wherein the phacoemulsification needle further comprises:
   a through hole located in the hollow shaft and extending from the exterior surface to the interior surface of the hollow shaft wherein the first over mold substantially fills the through hole.

3. The method of claim 1 wherein the first over mold has a rounded front edge located over the distal edge of the hollow shaft and a rounded trailing edge located on the exterior surface of the hollow shaft.

4. The method of claim 3 wherein the phacoemulsification needle further comprises:
   a second over mold located on the first over mold, the second over mold covering at least a portion of a periphery of an exterior surface of the first over mold, the second over mold covering the rounded front edge of the first over mold and terminating at the central bore.

5. The method of claim 4 wherein the second over mold is embedded in the first over mold such that the exterior surface of the first over mold is continuous with an exterior surface of the second over mold.

6. The method of claim 4 wherein the second over mold extends circumferentially around the entire perimeter of the exterior surface of the hollow shaft.

7. The method of claim 4 wherein the second over mold is made of silicone.

8. The method of claim 1 wherein the first over mold extends circumferentially around the entire perimeter of the exterior surface of the hollow shaft.

9. The method of claim 1 wherein the first over mold is made of a polymer.

* * * * *